United States Patent
Strahl et al.

(10) Patent No.: US 10,327,654 B2
(45) Date of Patent: Jun. 25, 2019

(54) DETECTING NEURONAL ACTION POTENTIALS USING A SPARSE SIGNAL REPRESENTATION

(71) Applicant: MED-EL Elektromedizinische Geraete GmbH, Innsbruck (AT)

(72) Inventors: Stefan Strahl, Innsbruck (AT); Konrad Schwarz, Innsbruck (AT); Philipp Spitzer, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 792 days.

(21) Appl. No.: 14/561,322

(22) Filed: Dec. 5, 2014

(65) Prior Publication Data

US 2015/0157226 A1 Jun. 11, 2015

Related U.S. Application Data

(60) Provisional application No. 61/912,648, filed on Dec. 6, 2013.

(51) Int. Cl.
*A61B 5/04* (2006.01)
*A61B 5/00* (2006.01)
(Continued)

(52) U.S. Cl.
CPC ...... *A61B 5/04001* (2013.01); *A61B 5/04845* (2013.01); *A61B 5/7246* (2013.01);
(Continued)

(58) Field of Classification Search
CPC ................................................ A61B 5/04845
See application file for complete search history.

(56) References Cited

U.S. PATENT DOCUMENTS

| 7,450,992 B1 | 11/2008 | Cameron |
| 2006/0256978 A1 | 11/2006 | Balan et al. |

FOREIGN PATENT DOCUMENTS

| WO | WO 2012/155185 A1 | 11/2012 |
| WO | WO 2012/155188 | 11/2012 |

OTHER PUBLICATIONS

International Searching Authority, International Search Report and Written Opinion—PCT/US14/68703, dated Mar. 5, 2015, 12 pages.
(Continued)

*Primary Examiner* — Daniel L Cerioni
*Assistant Examiner* — Yasmeen S Warsi
(74) *Attorney, Agent, or Firm* — Sunstein Kann Murphy & Timbers LLP

(57) ABSTRACT

A system and method detect neuronal action potential signals from tissue responding to electrical stimulation signals. A sparse signal space model for a set of tissue response recordings has a signal space separable into a plurality of disjoint component manifolds including a neural action potential (NAP) component manifold corresponding to tissue response to electrical stimulation signals. A response measurement module is configured to: i. map a tissue response measurement signal into the sparse signal model space to obtain a corresponding sparse signal representation, ii. project the sparse signal representation onto the NAP component manifold to obtain a sparse NAP component representation, iii. when the sparse NAP component representation is greater than a minimum threshold value, report and recover a detected NAP signal in the tissue response measurement signal.

8 Claims, 3 Drawing Sheets

(51) Int. Cl.
*A61B 5/0484* (2006.01)
*G06N 20/00* (2019.01)
*A61N 1/36* (2006.01)

(52) U.S. Cl.
CPC ........... *A61B 5/7264* (2013.01); *G06N 20/00* (2019.01); *A61B 5/4848* (2013.01); *A61B 5/6817* (2013.01); *A61N 1/36036* (2017.08)

(56) References Cited

OTHER PUBLICATIONS

Zhang, et al, "Reconstruction of Neural Action Potentials Using Signal Dependent Sparse Representations", *Circuits and Systems* (*ISCAS*), 2013 IEEE International Symposium, May 2013 (May 2013), pp. 1520-1523 [online], retrieved on Feb. 3, 2015. Retrieved from the Internet URL:http://ieeexplore.ieee.org/xpl/articleDetails.jsp?reload=true&arnumber=6572147 4 pages.
European Patent Office, Extended European Search Report, Application No. 14867314.8, 6 pages, dated Jul. 4, 2017.
Klein et al., "Robust Spectro-Temporal Reverse Correlation for the Auditory System: Optimizing Stimulus Design," Journal of Computational Neuroscience, vol. 9, pp. 85-111, 2000.
Vinje et al., "Sparse Coding and Decorrelation in Primary Visual Cortex During Natural Vision," Science, vol. 287, pp. 1273-1276, 2000.
Yu et al., "A joint sparse representation-based method for double-trial evoked potentials estimation," Computers in Biology and Medicine, vol. 43, pp. 2071-2078, 2013.

DETECTING NEURONAL ACTION POTENTIALS USING A SPARSE SIGNAL REPRESENTATION

This application claims priority from U.S. Provisional Patent Application 61/912,648, filed Dec. 6, 2013, which is incorporated herein by reference in its entirety.

TECHNICAL FIELD

The present invention relates to detecting neuronal action potential signals from tissue responding to electrical stimulation signals, especially for hearing implant systems such as cochlear implant systems.

BACKGROUND ART

Most sounds are transmitted in a normal ear as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is associated with the cochlea 104, a cochlear implant with an implanted stimulation electrode can electrically stimulate auditory nerve tissue with small currents delivered by multiple electrode contacts distributed along the electrode.

In some cases, hearing impairment can be addressed by a cochlear implant (CI), a brainstem-, midbrain- or cortical implant that electrically stimulates auditory nerve tissue with small currents delivered by multiple electrode contacts distributed along an implant electrode. For cochlear implants, the electrode array is inserted into the cochlea. For brainstem, midbrain and cortical implants, the electrode array is located in the auditory brainstem, midbrain or cortex, respectively.

FIG. 1 shows some components of a typical cochlear implant system where an external microphone provides an audio signal input to an external signal processor 111 which implements one of various known signal processing schemes. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, fine structure processing (FSP) and compressed analog (CA) signal processing.

The processed signal is converted by the external signal processor 111 into a digital data format, such as a sequence of data frames, for transmission by an external coil 107 into a receiving stimulator processor 108. Besides extracting the audio information, the receiver processor in the stimulator processor 108 may perform additional signal processing such as error correction, pulse formation, etc., and produces a stimulation pattern (based on the extracted audio information) that is sent through electrode lead 109 to an implanted electrode array 110. Typically, the electrode array 110 includes multiple stimulation contacts 112 on its surface that provide selective electrical stimulation of the cochlea 104.

Generally, there is a need to obtain data from the implanted components of a cochlear implant. Such data collection enables detection and confirmation of the normal operation of the device, and allows stimulation parameters to be optimized to suit the needs of individual recipients. This includes data relating to the response of the auditory nerve to stimulation, which is of particular relevance to the present invention. Thus, regardless of the particular configuration, cochlear implants generally have the capability to communicate with an external device such as for program upgrades and/or implant interrogation, and to read and/or alter the operating parameters of the device.

Typically, following the surgical implantation of a cochlear implant, the implant is fitted or customized to conform to the specific recipient demands. This involves the collection and determination of patient-specific parameters such as threshold levels (T levels) and maximum comfort levels (C levels) for each stimulation channel. Essentially, the procedure is performed manually by applying stimulation pulses for each channel and receiving an indication from the implant recipient as to the level and comfort of the resulting sound. For implants with a large number of channels for stimulation, this process is quite time consuming and rather subjective as it relies heavily on the recipient's Subjective impression of the stimulation rather than any objective measurement.

This approach is further limited in the case of children and prelingually or congenitally deaf patients who are unable to supply an accurate impression of the resultant hearing sensation, and hence fitting of the implant may be suboptimal. In such cases an incorrectly-fitted cochlear implant may result in the recipient not receiving optimum benefit from the implant, and in the cases of children, may directly hamper the speech and hearing development of the child. Therefore, there is a need to obtain objective measurements of patient-specific data, especially in cases where an accurate subjective measurement is not possible.

One proposed method of interrogating the performance of an implanted cochlear implant and making objective measurements of patient-specific data such as T and C levels is to directly measure the response of the auditory nerve to an electrical stimulus. To collect information about the electrode-nerve interface, a commonly used objective measurement is based on the measurement of Neural Action Potentials (NAPs) such as the electrically-evoked Compound Action Potential (eCAP), as described by Gantz et al., *Intraoperative Measures of Electrically Evoked Auditory Nerve Compound Action Potentials*, American Journal of Otology 15 (2):137-144 (1994), which is incorporated herein by reference. In this approach, the recording electrode is usually placed at the scala tympani of the inner ear. The overall response of the auditory nerve to an electrical stimulus is measured typically very close to the position of the nerve excitation. This neural response is caused by the super-position of single neural responses at the outside of the auditory nerve membranes. The response is characterized by the amplitude between the minimum voltage (this peak is called typically N1) and the maximum voltage (peak is called typically P2). The amplitude of the eCAP at the measurement position is between 10 µV and 1800 µV. One eCAP recording paradigm is a so-called "amplitude growth function," as described by Brown et al., *Electrically Evoked Whole Nerve Action Potentials In Ineraid Cochlear Implant Users: Responses To Different Stimulating Electrode Configurations And Comparison To Psychophysical Responses*, Journal of Speech and Hearing Research, vol. 39:453-467 (June 1996), which is incorporated herein by reference. This function is the relation between the amplitude of the stimulation pulse and the peak-to-peak voltage of the eCAP. Another clinically used recording paradigm is the so called "recovery function" in which stimulation is achieved with two pulses with varying interpulse intervals. The recovery function as the relation of the amplitude of the second eCAP and the interpulse interval allows conclusions to be drawn about the refractory properties and particular properties concerning the time resolution of the auditory nerve.

Detecting NAPs such as eCAPs is based on an analysis of an obtained measurement recording (R) which can be understood as a signal mixture containing the desired NAPs (A), artifacts due to the stimulation (B) and other sources (C) and noise (D). A linear model of this signal mixture is:

$$R = A + B + C + D$$

State-of-the-art NAP measurement systems apply special recording sequences to reduce the unwanted artifacts and the noise present during the measurement. The stimulation artifact (B) is partially removed from the recording (R) by different measurement paradigms such as "alternating stimulation" (Eisen M D, Franck K H: "Electrically Evoked Compound Action Potential Amplitude Growth Functions and HiResolution Programming Levels in Pediatric CII Implant Subjects." Ear & Hearing 2004, 25 (6):528-538; which is incorporated herein by reference in its entirety), "masker probe" (Brown C, Abbas P, Gantz B: "Electrically evoked whole-nerve action potentials: data from human cochlear implant users." The Journal of the Acoustical Society of America 1990, 88 (3):1385-1391; Miller C A, Abbas P J, Brown C J: An improved method of reducing stimulus artifact in the electrically evoked whole-nerve potential. Ear & Hearing 2000, 21 (4):280-290; both of which are incorporated herein by reference in their entireties), "tri-phasic stimulation" (Zimmerling M: "Messung des elektrisch evozierten Summenaktionspotentials des Hörnervs bei Patienten mit einem Cochlea-Implantat." In PhD thesis Universität Innsbruck, Institut für Angewandte Physik; 1999; Schoesser H, Zierhofer C, Hochmair E S. "Measuring electrically evoked compound action potentials using triphasic pulses for the reduction of the residual stimulation artefact," In: Conference on implantable auditory prostheses; 2001; both of which are incorporated herein by reference in their entireties), and "scaled template" (Miller C A, Abbas P J, Rubinstein J T, Robinson B, Matsuoka A, Woodworth G: Electrically evoked compound action potentials of guinea pig and cat: responses to monopolar, monophasic stimulation. Hearing Research 1998, 119 (1-2):142-154; which is incorporated herein by reference in its entirety). Artifacts due to other sources (C) are partially removed by a "zero amplitude template" (Brown et al. 2000). The noise (D) is reduced by repeated measurements, averaging over the repeated recordings reduces the noise level by $\sqrt{N}$ for N repetitions.

These special recording sequences result in a processed recording (R') with a reduced noise floor (D') and remaining artifacts (B' and C') which in most cases are reduced in amplitude. Some recording sequences also result in an altered NAP response (A'), for example the "masker probe" paradigm (Westen, A. A.; Dekker, D. M. T.; Briaire, J. J. & Frijns, J. H. M. "Stimulus level effects on neural excitation and eCAP amplitude." Hear Res, 2011, 280, 166-176; which is incorporated herein by reference in its entirety).

To automatically detect a NAP response in the resulting recording (R') one commonly used technique is known as "template matching" (SmartNRT as used by Advanced Bionics; Arnold, L. & Boyle, P. "SmartNRI: algorithm and mathematical basis." Proceedings of 8th EFAS Congress/10th Congress of the German Society of Audiology, 2007; which is incorporated herein by reference in its entirety). First an additional de-noising of the recording (R') is performed by calculating correlations with basis functions predefined by a principal component analysis and performing weighted summation, resulting in a recording (R") with reduced noise (see U.S. Pat. No. 7,447,549; which is incorporated herein by reference in its entirety). Then an artifact model ($B_{Model} + C_{Model}$) representing the sum of two decaying exponentials is fitted to this post-processed recording (R") and with a strength of response metric (SOR=(R"−$B_{Model} - C_{Model}$)/noise) a threshold is determined to detect a possible NAP (A) (U.S. Pat. No. 7,818,052; which is incorporated herein by reference in its entirety).

Another approach to automatically detect a NAP response in the resulting recording (R') is known as expert system (AutoNRT™ as used by Cochlear Ltd.; Botros, A.; van Dijk, B. & Killian, M. "AutoNRT™: An automated system that measures ECAP thresholds with the Nucleus® Freedom™ cochlear implant via machine intelligence" Artificial Intelligence in Medicine, 2007, 40, 15-28; which is incorporated herein by reference in its entirety). The expert system used is a combination of a template matching and a decision tree classifier (U.S. Patent Publication US 20080319508 A1; which is incorporated herein by reference in its entirety). The template matching classifier computes the correlation with a NAP (A) template and a NAP plus stimulation artifact (A+B) template. The decision tree uses the following six parameters:

N1-P1 amplitude for NAP typically latencies
noise level
ratio N1-P1 amplitude to noise level
correlation with NAP (A) template
correlation with NAP plus stimulation artifact (A+B) template
correlation between this measurement (R) and a previous measurement at a lower stimulation amplitude.

Two different decision tree classifiers were learned with a C5.0 decision tree algorithm. For the case where no NAP (A) was detected at lower stimulation levels, the stimulation level was increased and a decision tree with a low false positive rate was used to determine the presence of a NAP (A). For the case where a NAP (A) was detected, the stimulation level was reduced and a decision tree with a low overall error rate was used to evaluate the presence of a NAP (A).

An established working hypothesis is that neurosensory systems are performing a highly optimized signal analysis using a sparse representation (see for example B. Olshausen and D. Field, "Sparse coding of sensory inputs," Curr Opin Neurobiol, vol. 14, no. 4, pp. 481-487, 2004, incorporated herein by reference in its entirety). Such a signal model is important in the context of analysis, estimation and automatic detection of a signal. The earliest theoretical signal analysis model, proposed by Fourier (J. B. J. Fourier, Théorie analytique de la chaleur (The Analytical Theory of Heat). Paris: F. Didot, 1822, incorporated herein by reference in its entirety), analyzes the frequency content of a signal using the expansion of functions into a weighted sum of sinusoids. Gabor (D. Gabor, "Theory of communications," Journal of Institute of Electrical Engineers, vol. 93, no. III-26, pp. 429-457, 1946, incorporated herein by reference in its entirety) extended this signal model by using shifted and modulated time-frequency atoms which analyze the signal in the frequency as well as in the time dimension. The wavelet signal model, a further improvement presented by Morlet et al. (J. Morlet, G. Arens, I. Fourgeau, and D. Giard, "Wave propagation and sampling theory," Geophysics, vol. 47, no. 2, pp. 203-236, 1982, incorporated herein by reference in its entirety), uses time-frequency atoms that are scaled dependent on their center frequency. This yields an analysis of the time-frequency plane with a non-uniform tiling. However, the time-frequency atoms used in these signal models normally do not assume an underlying signal structure. As the performance of subsequent detection algorithms depends strongly on how well the fundamental features of a signal are captured, it is favorable to use time-frequency atoms that are specialized to the applied signal class and inherently exhibit the property of a sparse representation. To derive such a data dependent sparse signal-model, several algorithms have been proposed, for example, but not limited to: MOD (K. Engan, S. O. Aase, and J. H. Husøy, "Method of optimal directions for frame design", Proc. ICASSP, Vol. 5, pp. 2443-2446, 1999, incorporated herein by reference in its entirety) or K-SVD (U.S. Pat. No. 8,165,215, incorporated herein by reference in its entirety).

SUMMARY

Embodiments of the present invention are directed to a system and method to detect neuronal action potential signals from tissue responding to electrical stimulation signals. A sparse signal space model for a set of tissue response recordings has a signal space separable into a plurality of disjoint component manifolds including a neural action potential (NAP) component manifold corresponding to tissue response to electrical stimulation signals. A response measurement module is configured to: i. map a tissue response measurement signal into the sparse signal model space to obtain a corresponding sparse signal representation, ii. project the sparse signal representation onto the NAP component manifold to obtain a sparse NAP component representation, iii. report a detected NAP signal in the tissue response measurement signal when the signal energy of the sparse NAP component representation is greater than a minimum threshold value.

Based on the signal mixture R=A+B+C+D (as described above), the response measurement module may be further configured to project, recover and report at least one other detected signal for at least one other component manifold in the model signal space, such as a stimulation artifact signal B. The detected NAP signal A may specifically be an electrically-evoked compound action potential (eCAP) signal. The sparse signal space model may specifically be a MOD or K-SVD trained model. The NAP component manifold may be constrained by a NAP signal model. And the minimum threshold value may be a fixed constant value, or a variable function of one or more components in the tissue response measurement signal.

DETAILED DESCRIPTION

Instead of using complex detection algorithms such as template matching or machine-learned expert systems such as decision tree classifiers to recognize possible NAPs directly in the tissue response measurement recording, embodiments of the present invention maps the recording into a sparse signal space using for example a MOD or K-SVD trained signal model to obtain a sparse signal representation which allows a robust and computationally inexpensive signal detection and classification of possible NAPs and signal artifacts within this signal space.

Figure 1:
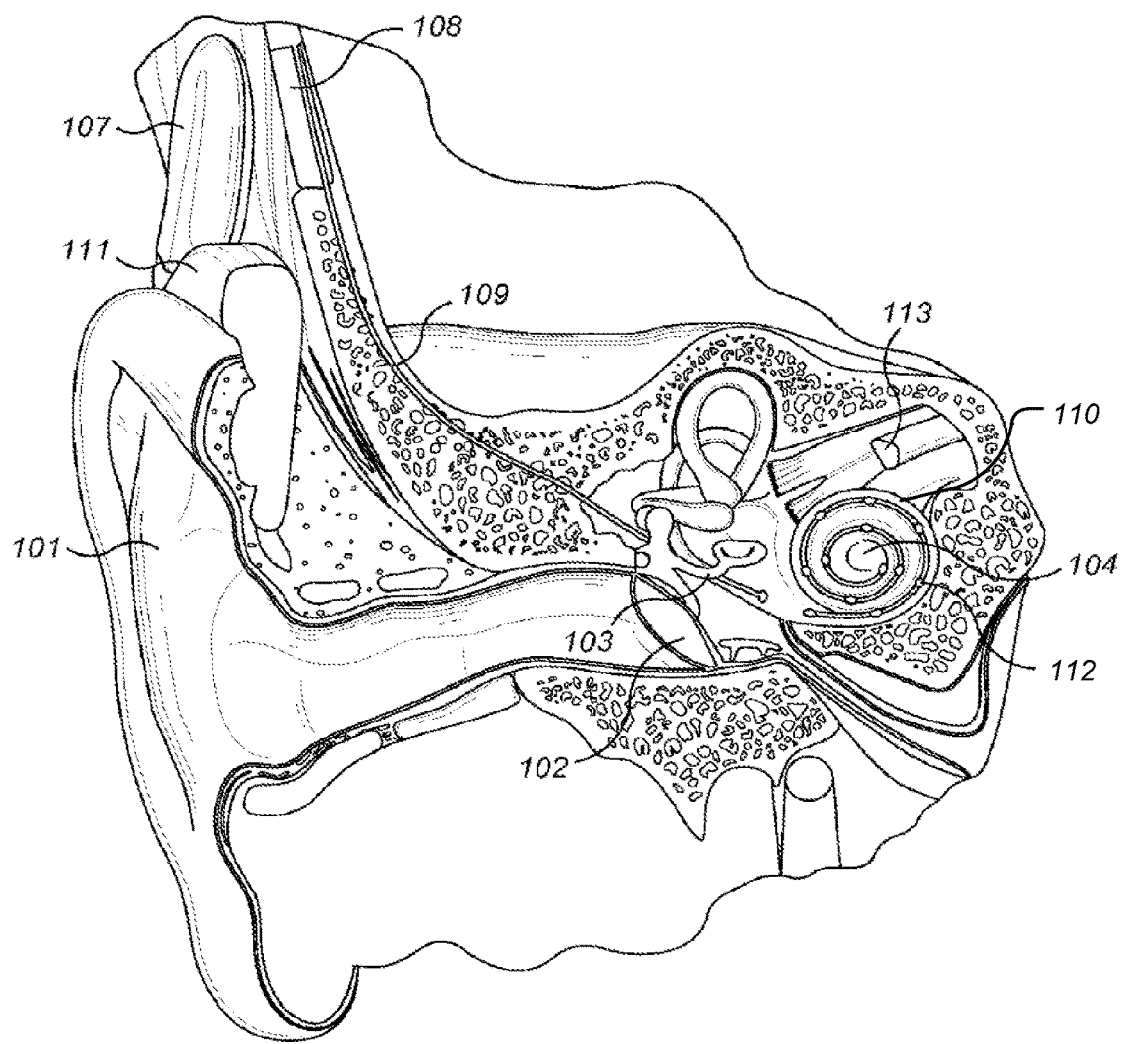
FIG. 1 shows anatomical structures of a human ear having a cochlear implant system.
Figure 2:
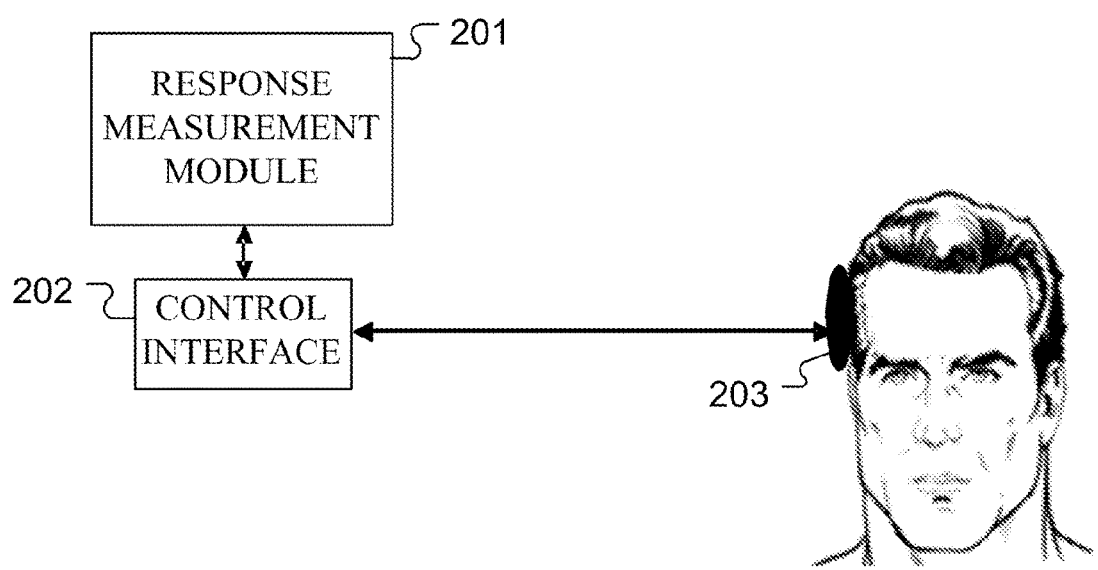
FIG. 2 shows various components in a system for measuring neural action potential (NAP) signals from tissue responding to electrical stimulation signals according to one specific embodiment of the present invention.
Figure 3:
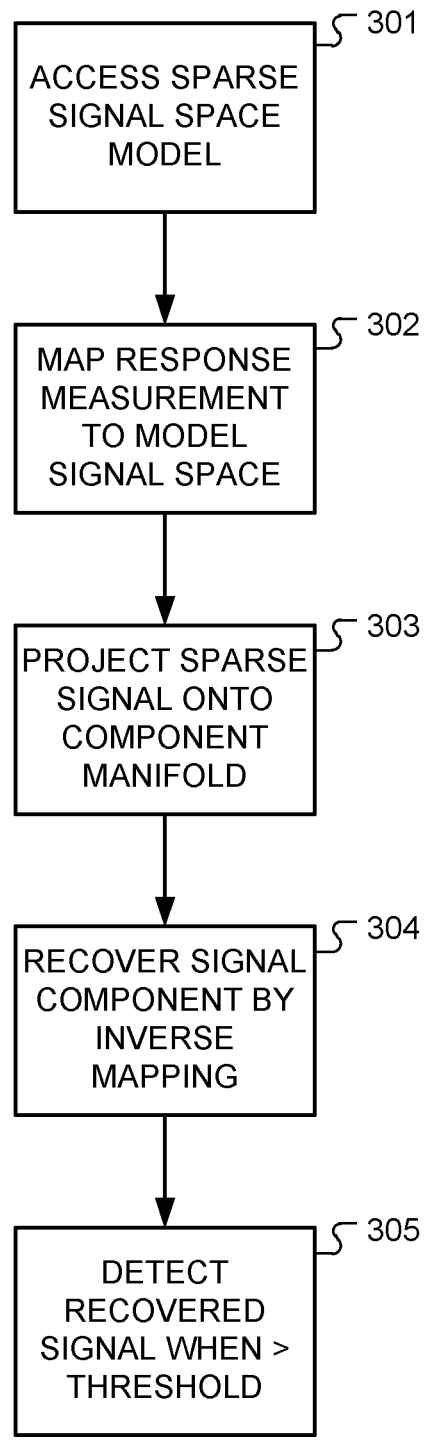
FIG. 3 shows the functional steps in a method of measuring neural action potential (NAP) signals from tissue responding to electrical stimulation signals according to one specific embodiment of the present invention.

FIG. 2 shows various functional blocks in a system for measuring neural action potential (NAP) signals from tissue responding to electrical stimulation signals and FIG. 3 shows the functional steps in a method of measuring neural action potential (NAP) signals from tissue responding to electrical stimulation signals according to embodiments of the present invention. Response measurement module 201 contains a combination of software and hardware for generating electrical stimulation pulses for the target neural tissue and recording and analyzing the NAPs. For example, the response measurement module 201 may be based on a Research Interface Box (RIB) II system manufactured at the University of Technology Innsbruck, Austria which may include a personal computer equipped with a National Instruments digital IO card, a RIB II isolation box, and a communications cable between IO card and RIB II box. The electrical stimulation pulses are transmitted from the response measurement module 201 through a control interface 202 to an external transmitter 203 which transmits them through the skin to implant electrodes to the target neural tissue. The NAP responses are recorded at the implant electrodes and transmitted via the external transmitter 203 through the control interface 202 to the response measurement module 201.

Initially, a sparse signal space model S is trained for a set of tissue response recordings in a form r=a+b+c+d, where r∈ $\mathbb{R}^N$ is an individual tissue response recording representing a signal mixture, a∈ $\mathbb{R}^N$ is a neural action potential (NAP) component of r, b∈ $\mathbb{R}^N$ is a stimulation artifact component of r, c∈ $\mathbb{R}^N$ is an other source artifact component of r, d∈ $\mathbb{R}^N$ is a noise component of r, where the sparse signal model S: $\mathbb{R}^N \to \mathbb{R}^M$ such that a sparse signal representation $r_s = f_s(r)$ with $\min_{r_s} \|r_s\|_0$, and i. $a_s = f_s(a)$, $a_s \in A = \mathbb{R}^\alpha \subset S$, $\alpha < M$,
ii. $b_s = f_s(b)$, $b_s \in B = \mathbb{R}^\beta \subset S$, $\beta < M$,
iii. $c_s = f_s(c)$, $c_s \in C = \mathbb{R}^\gamma \subset S$, $\gamma < M$, with A∩B=∅, A∩C=∅, B∩C=∅ and α+β+γ<M. The minimum of a function with respect to a variable x is denoted as $\min_x f(x)$. The L0 norm, which corresponds to the number of non-zero elements, is denoted as $\|\cdot\|_0$. That is, the sparse signal space S is separable into multiple disjoint component manifolds (A, B, C). Training of the sparse signal space model S only needs to be done once with a sufficiently large number of known tissue response recordings and for each of the component manifolds.

The response measurement module 201 then accesses the sparse signal space model, step 301, and derives a sparse signal representation $r_s$ for the tissue response measurement signal r using the predefined sparse signal space model S, step 302. The response measurement module 201 then projects the sparse representation $r_s$ onto all predefined manifolds, step 303; for example, projecting the sparse representation $r_s$ onto the NAP component manifold A to obtain a sparse representation $a_s$ of a possible NAP, step 304. The response measurement module 201 then reports if a predefined signal was present in the tissue response measurement signal r when the signal energy of the sparse representation is greater than a minimum threshold value energy; e.g., a NAP component a is reported if the derived $\|a_s\| > a_{thr}$, step 305.

If the stimulation artifact signal b is desired, then the response measurement module 201 projects sparse representation $r_s$ into the stimulation artifact manifold B, and likewise for source artifact component signal c and the noise component d. This system allows a measurement analysis using just computationally inexpensive projections. That reduces the computational complexity considerably, and furthermore, operating within the sparse signal space is very efficient since many of the signal coefficients are zero. Furthermore this system mimics the signal processing of neurosensory systems that are optimized to perform in a robust manner.

Once the projection into the predefined sparse signal space has been done, the needed energy to detect a component signal a, b, c or d can be calculated or looked up in a table. For example, a look up table may store the energy for the associated NAP signal of the NAP component manifold in the sparse signal space. If the energy level of the signal component is above some minimum threshold value, then the NAP signal has been recovered. This energy threshold may be a fixed level, or in some embodiments, it may be a variable function of one or more of the components in the tissue response measurement signal. For example, if the stimulation artifact b has a relatively high signal energy, that suggests that the reference electrode contact has high impedance and may need to be checked. It also suggests that the estimate of the NAP signal needs to be done very carefully, and so the energy threshold for the NAP signal may accordingly be increased.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments also can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for detecting neuronal action potential signals from tissue responding to electrical stimulation signals, and providing stimulation to address hearing impairment, the method comprising:

transmitting, via an external transmitter, stimulation pulses to a cochlear implant, the cochlear implant including electrodes for providing the stimulation pulses to neural tissue and detecting a tissue response measurement signal;

receiving, via the external transmitter, the tissue response measurement signal from the cochlear implant;

using a computer to perform the steps of:

accessing a sparse signal space model for a set of tissue response recordings, the model having a signal space separable into a plurality of disjoint component manifolds including:

a neural action potential (NAP) component manifold corresponding to tissue response to electrical stimulation signals, a stimulation artifact component manifold corresponding to artifacts due to the electrical stimulation signals, a source artifact component manifold corresponding to artifacts due to sources other than the electrical stimulation signals, and a noise artifact component manifold;

mapping the tissue response measurement signal into the model signal space to obtain a corresponding sparse signal representation;

projecting the sparse signal representation onto the NAP component manifold to obtain a sparse NAP component representation; and when the sparse NAP component representation is greater than a minimum threshold value, reporting a detected NAP signal in the tissue response measurement signal; and determining an operating parameter for the cochlear implant based on the detected NAP signal;

transmitting, via the external transmitter, the operating parameter to the cochlear implant; and providing, by the cochlear implant, stimulation pulses to the electrodes, the pulses based, at least in part, on the operating parameter.

2. The method according to claim 1, further comprising: reperforming the steps of projecting, recovering and reporting for at least one other component manifold in the model signal space.

3. The method according to claim 2, wherein the at least one other component manifold includes a stimulation signal artifact component manifold and the detected signal is a stimulation artifact signal.

4. The method according to claim 1, wherein the detected NAP signal is an electrically-evoked compound action potential (eCAP) signal.

5. The method according to claim 1, wherein the sparse signal space model is a MOD or K-SVD trained model.

6. The method according to claim 1, wherein the NAP component manifold is constrained by a NAP signal model.

7. The method according to claim 1, wherein the minimum threshold value is a fixed constant value.

8. The method according to claim 1, wherein the minimum threshold value is a variable function of one or more components in the tissue response measurement signal.

\* \* \* \* \*